US006277156B1

United States Patent
Audousset

(10) Patent No.: US 6,277,156 B1
(45) Date of Patent: *Aug. 21, 2001

(54) OXIDATION DYEING COMPOSITION FOR KERATIN FIBRES COMPRISING 2-CHLORO-6-METHYL-3-AMINOPHENOL AND AN OXIDATION BASE, AND DYEING METHOD

(75) Inventor: Marie-Pascale Audousset, Asnières (FR)

(73) Assignee: L'Oréal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,498
(22) PCT Filed: Jul. 16, 1998
(86) PCT No.: PCT/FR98/01562
 § 371 Date: Jul. 6, 1999
 § 102(e) Date: Jul. 6, 1999
(87) PCT Pub. No.: WO99/11230
 PCT Pub. Date: Mar. 11, 1999

(30) Foreign Application Priority Data

Sep. 1, 1997 (FR) .................................................. 97 10854

(51) Int. Cl.⁷ ...................................................... A61K 7/13
(52) U.S. Cl. .......................... 8/407; 8/405; 8/406; 8/408; 8/409; 8/410; 8/411; 8/421; 8/412
(58) Field of Search ............................... 8/407, 408, 409, 8/410, 412, 421, 416

(56) References Cited

U.S. PATENT DOCUMENTS

| | | | |
|---|---|---|---|
| 3,712,790 | 1/1973 | Kalopissis et al. | 8/409 |
| 3,907,799 | 9/1975 | O'Brien et al. | 544/281 |
| 4,035,422 | 7/1977 | Kalopissis et al. | 564/167 |
| 4,268,264 * | 5/1981 | Grollier et al. | 8/410 |
| 4,745,652 | 5/1988 | Rose et al. | 8/409 |
| 4,838,893 | 6/1989 | Rose et al. | 8/409 |
| 4,904,275 * | 2/1990 | Grollier | 8/408 |
| 5,443,596 * | 8/1995 | Junino et al. | 8/442 |
| 5,534,036 | 7/1996 | Junino et al. | 8/411 |
| 5,534,037 | 7/1996 | Junino et al. | 8/411 |
| 5,672,759 | 9/1997 | Junino et al. | 564/440 |
| 5,703,266 * | 12/1997 | Lagrange et al. | 558/440 |
| 5,735,909 | 4/1998 | Maubru | 8/412 |
| 5,752,983 * | 5/1998 | Audousset et al. | 8/409 |

FOREIGN PATENT DOCUMENTS

| | | |
|---|---|---|
| 1 939 063 | 2/1970 | (DE) . |
| 2 359 399 | 6/1975 | (DE) . |
| 3 016 008 | 10/1981 | (DE) . |
| 3 843 892 | 6/1990 | (DE) . |
| 4 122 748 | 1/1993 | (DE) . |
| 4 133 957 | 4/1993 | (DE) . |
| 4 205 329 | 8/1993 | (DE) . |
| 4 344 551 | 6/1995 | (DE) . |
| 19 535 340 | 3/1997 | (DE) . |
| 19 543 988 | 5/1997 | (DE) . |
| 0 039 030 | 11/1981 | (EP) . |
| 0 063 736 | 11/1982 | (EP) . |
| 0 256 468 | 2/1988 | (EP) . |
| 355364 * | 2/1990 | (EP) . |
| 0 591 059 | 4/1994 | (EP) . |
| 0 628559 | 12/1994 | (EP) . |
| 0 728 465 | 8/1996 | (EP) . |
| 2 586 913 | 3/1987 | (FR) . |
| 2 687 399 | 8/1993 | (FR) . |
| 2 733 749 | 11/1996 | (FR) . |
| 1 026 978 | 4/1966 | (GB) . |
| 1 153 196 | 5/1969 | (GB) . |
| 63-169571 | 7/1988 | (JP) . |
| 3-33495 | 2/1991 | (JP) . |
| WO 90/12562 | 11/1990 | (WO) . |
| WO 92/04883 | 4/1992 | (WO) . |
| WO 94/08969 | 4/1994 | (WO) . |
| WO 94/08970 | 4/1994 | (WO) . |
| WO 94/27564 | 12/1994 | (WO) . |
| WO 96/15765 | 5/1996 | (WO) . |
| WO 96/15766 | 5/1996 | (WO) . |
| WO 97/11674 | 4/1997 | (WO) . |
| 97/31886 * | 9/1997 | (WO) . |

OTHER PUBLICATIONS

English language translation of EP 39,030, Henkel, pp. 1–13, Nov. 1981.*

CAPLUS Abstract of DE 19545854, Wella, Jun. 1997.*

Ermitas Alcalde et al., "Etude de la réaction du β–aminocrotonitrile et du α–formyl phénylacétonitrile avec l'hydrazine: synthése d'amino–7 pyrazolo[1,5–α]pyrimidines", Journal of Heterocyclic Chemistry, vol. 11, No. 3, Jun. 1974, pp. 423–429.

Nadia S. Ibrahim et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Alexander McKillop et al., "Reaction of Hydrazine with β–Aminocrotononitrile: Synthesis of 2,7–Dimethyl–5–Aminopyrazolo [1,5–β]pyrimidine", Heterocycles, vol. 6, Nos. 9, 10, 1977, pp. 1355–1360, (No month available).

(List continued on next page.)

Primary Examiner—Margaret Einsmann
Assistant Examiner—Aniy K. Puri
(74) Attorney, Agent, or Firm—Finnegan, Henderson, Farabow, Garrett & Dunner, L.L.P.

(57) ABSTRACT

The subject-matter of the present invention is a composition for the oxidation dyeing of keratinous fibres, in particular of human keratinous fibres, such as hair, comprising 2-chloro-6-methyl-3-aminophenol as coupler, in combination with at least one suitably selected oxidation base, and the dyeing process employing this composition with an oxidizing agent.

44 Claims, No Drawings

OTHER PUBLICATIONS

Thomas Novinson et al., "Synthesis and Antifungal Properties of certain 7–Alkylaminopyrazolo[1,5–α]pyrimidines", Journal of Medicinal Chemistry, vol. 20, No. 2, Feb. 1977, pp. 296–299.

Vishnu J. Ram et al., "Synthesis of bioisosteric pyrazolo[1,5–α]pyrimidines as leishmanicides", Indian Journal of Chemistry, vol. 34B, Jun. 1995, pp. 514–420.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480, (No month available).

Robert H. Springer et al., "Synthesis and Enzymica Activity of 6–Carbethoxy–and 6–Ethoxy–3,7–disubstituted–pyrazolo[1,5–α]pyrimidines and Related Derivatives as Adenosine Cyclic 3',5'–Phosphate Phosphodiesterase Inhibitors", Journal of Medicinal Chemistry, vol. 25, No. 3, Mar. 1982, pp. 235–242.

English language Derwent Abstract of DE 2 359 399, Jun. 1975.

English language Derwent Abstract of DE 3 016 008, Oct. 1981.

English language Derwent Abstract of DE 3 843 892, Jun. 1990.

English language Derwent Abstract of DE 4 122 748, Jan. 1993.

English language Derwent Abstract of DE 4 133 957, Apr. 1993.

English language Derwent Abstract of DE 4 205 329, Aug. 1993.

English language Derwent Abstract of DE 4 344 551, Jun. 1995.

English language Derwent Abstract of DE 19 535 340, Mar. 1997.

English language Derwent Abstract of DE 19 543 988, May 1997.

English language Derwent Abstract of EP 0 039 030, Nov. 1981.

English language Derwent Abstract of FR 2 586 913, Mar. 1987.

English language Derwent Abstract of FR 2 733 749, Nov. 1996.

English language Derwent Abstract of JP 2019576, Jan. 1990.

English language Derwent Abstract of JP 03–033495, Feb. 1991.

* cited by examiner

OXIDATION DYEING COMPOSITION FOR KERATIN FIBRES COMPRISING 2-CHLORO-6-METHYL-3-AMINOPHENOL AND AN OXIDATION BASE, AND DYEING METHOD

The subject-matter of the present invention is a composition for the oxidation dyeing of keratinous fibres, in particular of human keratinous fibres, such as hair, comprising 2-chloro-6-methyl-3-aminophenol as coupler, in combination with at least one suitably selected oxidation base, and the dyeing process employing this composition with an oxidizing agent.

It is known to dye keratinous fibres and in particular human hair with dyeing compositions comprising oxidation dye precursors, in particular ortho- or para-phenylenediamines, ortho- or para-aminophenols, or heterocyclic compounds, such as pyrimidine derivatives, generally known as oxidation bases. Oxidation dye precursors or oxidation bases are colourless or weakly coloured compounds which, in combination with oxidizing substances, can give rise, by an oxidative coupling process, to coloured and colouring compounds.

It is also known that it is possible to vary the shades obtained with oxidation bases by combining them with suitably chosen couplers or colouring modifiers, it being possible for the latter in particular to be chosen from aromatic meta-diamines, meta-aminophenols, meta-diphenols and certain heterocyclic compounds.

The variety of the molecules involved as oxidation bases and couplers makes it possible to obtain a rich palette of colours.

The so-called "permanent" colouring obtained by virtue of these oxidation dyes has, however, to satisfy a certain number of requirements. Thus, it must be without disadvantage toxicologically and it must make it possible to obtain shades with the desired intensity and behave well in the face of external agents (light, bad weather, washing, permanent waving, perspiration or rubbing).

The dyes must also make it possible to cover white hair and, finally, be as non-selective as possible, that is to say make it possible to obtain the smallest possible difference in colouring along the same keratinous fibre, which can in fact be differently sensitized (i.e. damaged) between its tip and its root.

Provision has already been made, in particular in German Patent Application DE 3,016,008, for compositions for the oxidation dyeing of keratinous fibres comprising, as coupler, 2-chloro-6-methyl-3-aminophenol or 2-methyl-5-chloro-3-aminophenol in combination with oxidation bases conventionally used for oxidation dyeing, such as, for example, certain para-phenylenediamines, para-aminophenol or tetraaminopyrimidine. However, such compositions are not entirely satisfactory, in particular from the viewpoint of the behaviour of the colourings obtained with respect to various attacks which hair can be subjected to and in particular with respect to shampoos and permanent deformations.

Provision has also been made, in Patent Applications WO 96/15765 and WO 96/15766, for compositions for the oxidation dyeing of keratinous fibres comprising the specific combination of 2-chloro-6-methyl-3-aminophenol as coupler and of specific oxidation bases, such as 2-(β-hydroxyethyl)-para-phenylenediamine or certain specific para-aminophenols, such as, for example, 3-methyl-4-aminophenol, 2-allyl-4-aminophenol or 2-aminomethyl-4-aminophenol. However, such compositions are not entirely satisfactory either, in particular from the viewpoint of the strength of the colourings obtained.

The Applicant Company has now just discovered that it is possible to obtain powerful novel dyes which are particularly resistant to the various attacks which hair can be subjected to by combining 2-chloro-6-methyl-3-aminophenol and at least one suitably selected oxidation base.

This discovery is at the basis of the present invention.

The first subject-matter of the invention is therefore a composition for the oxidation dyeing of keratinous fibres and in particular of human keratinous fibres, such as hair, characterized in that it comprises, in a medium appropriate for dyeing:

2-chloro-6-methyl-3-aminophenol and/or at least one of its addition salts with an acid, as coupler;
and at least one oxidation base chosen from:
(a) the para-phenylenediamines of following formula (I) and their addition salts with an acid:

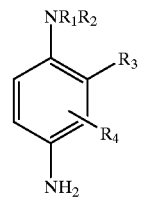

in which:
$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted by a nitrogenous, phenyl or 4'-aminophenyl group;
$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted by a nitrogenous group;
$R_3$ represents a hydrogen atom, a $C_1$–$C_4$ alkyl radical, a $C_1$–$C_4$ monohydroxyalkoxy radical, a $C_1$–$C_4$ mesylaminoalkoxy radical, a $C_1$–$C_4$ acetylaminoalkoxy radical, a $C_1$–$C_4$ carbamoylaminoalkoxy radical or a $C_1$–$C_4$ alkyl radical substituted by a nitrogenous group;
$R_4$ represents a hydrogen atom or a $C_1$–$C_4$ alkyl radical;
it being understood that:
at least one of the $R_1$, $R_2$, $R_3$ and $R_4$ radicals is other than a hydrogen atom,
when the $R_1$, $R_2$ and $R_4$ radicals simultaneously represent a hydrogen atom, then the $R_3$ radical is other than a methyl radical,
when the $R_1$, $R_2$ and $R_3$ radicals simultaneously represent a hydrogen atom and when the $R_4$ radical occupies the 6 position, then $R_4$ is other than a methyl radical,
when one of the $R_1$ and $R_2$ radicals represents a $C_1$–$C_4$ alkyl radical or a $C_1$–$C_4$ monohydroxyalkyl radical and when the other $R_1$ or $R_2$ radical represents a hydrogen atom, then at least one of the $R_3$ and $R_4$ radicals is other than a hydrogen atom;
when $R_1$ and $R_2$ simultaneously represent a $C_1$–$C_4$ monohydroxyalkyl radical, then at least one of the $R_3$ and $R_4$ radicals is other than a hydrogen atom;
(b) the following double bases of formula (II) and their addition salts with an acid:

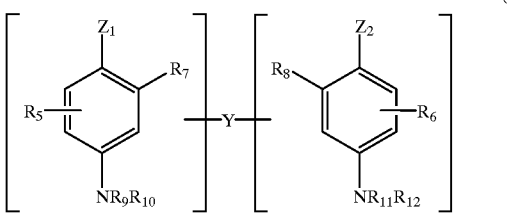

in which:
- $Z_1$ and $Z_2$, which are identical or different, represent a hydroxyl or —$NH_2$ radical which can be substituted by a $C_1$–$C_4$ alkyl radical or by a connecting arm Y;
- the connecting arm Y represents a linear or branched alkylene chain comprising from 1 to 14 carbon atoms which can be interrupted by one or more nitrogenous groups and/or by one or more heteroatoms, such as oxygen, sulphur or nitrogen atoms, and which is optionally substituted by one or more hydroxyl or $C_1$–$C_6$ alkoxy radicals;
- $R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a connecting arm Y;
- $R_7$, $R_8$, $R_9$, $R_{10}$, $R_{11}$ and $R_{12}$, which are identical or different, represent a hydrogen atom, a connecting arm Y or a $C_1$–$C_4$ alkyl radical;

it being understood that the compounds of formula (II) only comprise a single connecting arm Y per molecule;

(c) the pyrazolo[1,5-a]pyrimidines of following formula (III), their addition salts with an acid or with a base and their tautomeric forms, when a tautomeric equilibrium exists:

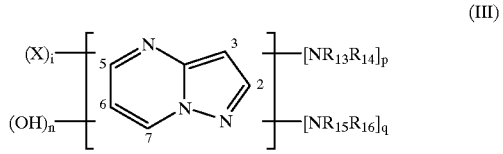

in which:
- $R_{13}$, $R_{14}$, $R_{15}$ and $R_{16}$, which are identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a ($C_1$–$C_4$)alkoxy($C_1$–$C_4$)alkyl radical, a $C_1$–$C_4$ aminoalkyl radical (it being possible for the amine to be protected by an acetyl, amido or sulphonyl radical), a ($C_1$–$C_4$)alkylamino($C_1$–$C_4$)alkyl radical, a di[($C_1$–$C_4$)alkyl]amino($C_1$–$C_4$)alkyl radical (it being possible for the dialkyl radicals to form a carbonaceous ring or a heterocycle with 5 or 6 ring members) or a hydroxy($C_1$–$C_4$)alkyl- or di[hydroxy($C_1$–$C_4$)alkyl]amino($C_1$–$C_4$)alkyl radical;
- the X radicals, which are identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a ($C_1$–$C_4$)alkylamino($C_1$–$C_4$)alkyl radical, a di[($C_1$–$C_4$)alkyl]amino($C_1$–$C_4$)alkyl radical (it being possible for the dialkyls to form a carbonaceous ring or a heterocycle with 5 or 6 ring members), a hydroxy($C_1$–$C_4$)alkyl- or di[hydroxy($C_1$–$C_4$)alkyl]amino($C_1$–$C_4$)alkyl radical, an amino radical, a ($C_1$–$C_4$)alkyl- or di[($C_1$–$C_4$)alkyl] amino radical, a halogen atom, a carboxylic acid group or a sulphonic acid group;
- i has the value 0, 1, 2 or 3;
- p has the value 0 or 1;
- q has the value 0 or 1;
- n has the value 0 or 1;

with the proviso that:
- the sum p+q is other than 0;
- when p+q is equal to 2, then n has the value 0 and the $NR_{13}R_{14}$ and $NR_{15}R_{16}$ groups occupy the (2,3), (5,6), (6,7), (3,5) or (3,7) positions;
- when p+q is equal to 1, then n has the value 1 and the $NR_{13}R_{14}$ (or $NR_{15}R_{16}$) group and the OH group occupy the (2,3), (5,6), (6,7), (3,5) or (3,7) positions;

d) ortho-aminophenols;
e) diaminopyridines;

the said composition being devoid of an additional coupler which would be chosen from 4-hydroxyindoline, 6-hydroxyindoline and their addition salts with an acid.

The oxidation dyeing composition in accordance with the invention makes it possible to obtain powerful colourings with varied shades which are not very selective and which exhibit excellent properties of resistance both with respect to atmospheric agents, such as light and bad weather, and with respect to perspiration and various treatments which hair can be subjected to (shampoos, permanent deformations). These properties are particularly noteworthy, in particular as regards the resistance of the colourings with respect to shampoos and permanent deformations.

Mention may in particular be made, among the $C_1$–$C_4$ alkyl and $C_1$–$C_4$ alkoxy radicals of the above formulae (I), (II) and (III), of the methyl, ethyl, propyl, methyloxy and ethyloxy radicals.

Mention may in particular be made, among the nitrogenous groups of the above formulae (I) and (II), of the amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Mention may more particularly be made, among the para-phenylenediamines of above formula (I) which can be used as oxidation base in the dyeing compositions in accordance with the invention, of 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-1-(N,N-diethylamino)-3-methylbenzene, 4-amino-1-(N,N-bis(β-hydroxyethyl)amino)-3-methylbenzene, 2-isopropyl-para-phenylenediamine, 2-n-propyl-para-phenylenediamine, 2-(β-hydroxyethyloxy)-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(β-methoxyethyl)amino-para-phenylenediamine, 2-(β-acetylaminoethyloxy)-para-phenylenediamine and their addition salts with an acid.

Preference is more particularly given, among the para-phenylenediamines of above formula (I), to 2,6-dimethyl-para-phenylenediamine, 2-n-propyl-para-phenylenediamine, 2-(β-hydroxyethyloxy)-para-phenylenediamine, N-(β-methoxyethyl)amino-para-phenylenediamine, 2-(β-acetylaminoethyloxy)-para-phenylenediamine and their addition salts with an acid.

Mention may more particularly be made, among the double bases of above formula (II) which can be used as oxidation base in the dyeing compositions in accordance with the invention, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine and their addition salts with an acid.

N,N'-Bis(β-hydroxyethyl)-N,N'-bis(4'-aminophenyl)-1,3-diaminopropanol and its addition salts with an acid are particularly preferred among these bis-phenylalkylenediamines of formula (II).

When the pyrazolo[1,5-a]pyrimidines of above formula (III) are such that they comprise a hydroxyl group on one of the 2, 5 or 7 positions α to a nitrogen atom, there exists a tautomeric equilibrium represented, for example, by the following scheme:

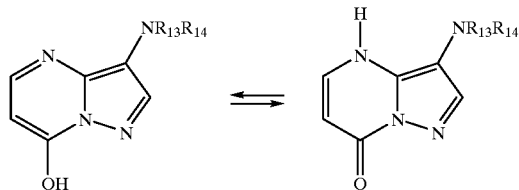

Mention may in particular be made, among the pyrazolo [1,5-a]pyrimidines of formula (III) which can be used as oxidation base in the compositions in accordance with the invention, of:

pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxyethyl)amino]ethanol;
2-[(7-aminopyrazolo[1,5-a]pyrimidin-3-yl)(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and their addition salts and their tautomeric forms, when there exists a tautomeric equilibrium.

The pyrazolo[1,5-a]pyrimidines of formula (III) in accordance with the invention can be prepared by cyclization from an aminopyrazole according to the syntheses disclosed in the following references:

EP 628,559, Beiersdorf-Lilly
R. Vishdu and H. Navedul, Indian J. Chem., 34b (6), 514, 1995.
N. S. Ibrahim, K. U. Sadek and F. A. Abdel-Al, Arch. Pharm., 320, 240, 1987.
R. H. Springer, M. B. Scholten, D. E. O'Brien, T. Novinson, J. P. Miller and R. K. Robins, J. Med. Chem., 25, 235, 1982.
T. Novinson, R. K. Robins and T. R. Matthews, J. Med. Chem., 20, 296, 1977.

U.S. Pat. No. 3,907,799, ICN Pharmaceuticals.

The pyrazolo[1,5-a]pyrimidines of formula (III) in accordance with the invention can also be prepared by cyclization from hydrazine according to the syntheses described in the following references:

A. McKillop and R. J. Kobilecki, Heterocycles, 6 (9), 1355, 1977.
E. Alcade, J. De Mendoza, J. M. Marcia-Marquina, C. Almera and J. Elguero, J. Heterocyclic Chem., 11 (3), 423, 1974.
K. Saito, I. Hori, M. Higarashi and H. Midorikawa, Bull. Chem. Soc. Japan, 47 (2), 476, 1974.

Mention may more particularly be made, among the ortho-aminophenols which can be used as oxidation base in the dyeing compositions in accordance with the invention, of 2-aminophenol, 2-amino-5-methylphenol, 2-amino-6-methylphenol, 5-acetamido-2-aminophenol and their addition salts with an acid.

Mention may more particularly be made, among the diaminopyridines which can be used as oxidation base in the dyeing compositions in accordance with the invention, of the compounds disclosed, for example, in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine and their addition salts with an acid.

2-Chloro-6-methyl-3-aminophenol and/or the addition salt or salts with an acid preferably represent from 0.0001 to 5% by weight approximately to the total weight of the dyeing composition and more preferably still from 0.005 to 3% by weight approximately of this weight.

The oxidation base or bases in accordance with the invention and/or their addition salts with an acid preferably represent from 0.0005 to 12% by weight approximately of the total weight of the dyeing composition and more preferably still from 0.005 to 6% by weight approximately of this weight.

The dyeing compositions in accordance with the invention can comprise other couplers other than 2-chloro-6-methyl-3-aminophenol and/or direct dyes, in particular for modifying the shades or enriching them with highlights.

The addition salts with an acid which can be used in the context of the dyeing compositions of the invention (oxidation bases and couplers) are generally chosen in particular from hydrochlorides, hydrobromides, sulphates and tartrates, lactates and acetates. The addition salts with a base which can be used in the context of the dyeing compositions of the invention (oxidation bases) are in particular those obtained with sodium hydroxide, potassium hydroxide, ammonia or amines.

The medium appropriate for dyeing (or vehicle) is generally composed of water or of a mixture of water and of at least one organic solvent, in order to dissolve the compounds which would not be sufficiently soluble in water. Mention may be made, for example, as organic solvent, of lower $C_1$–$C_4$ alkanols, such as ethanol and isopropanol, glycerol, glycols and glycol ethers, such as 2-butoxyethanol, propylene glycol, propylene glycol monomethyl ether, diethylene glycol monoethyl ether and diethylene glycol monomethyl ether, and aromatic alcohols, such as benzyl alcohol or phenoxyethanol, the analogous products and their mixtures.

The solvents can be present in proportions preferably of between 1 and 40% by weight approximately with respect to the total weight of the dyeing composition and more preferably still between 5 and 30% by weight approximately.

The pH of the dyeing composition in accordance with the invention is generally between 3 and 12 approximately and more preferably still between 5 and 11 approximately. It can be adjusted to the desired value by means of acidifying or basifying agents commonly used in dyeing keratinous fibres.

Mention may be made, among acidifying agents, by way of example, of inorganic or organic acids, such as hydrochloric acid, orthophosphoric acid, carboxylic acids, such as tartaric acid, citric acid or lactic acid, or sulphonic acids.

Mention may be made, among basifying agents, by way of example, of aqueous ammonia, alkaline carbonates, alkanolamines, such as mono-, di- and triethanolamines, and their derivatives, sodium hydroxide, potassium hydroxide and the compounds of following formula (IV):

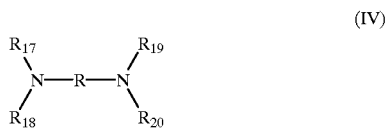

(IV)

in which R is a propylene residue optionally substituted by a hydroxyl group or a $C_1$–$C_4$ alkyl radical; and $R_{17}$, $R_{18}$, $R_{19}$ and $R_{20}$, which are identical or different, represent a hydrogen atom or a $C_1$–$C_4$ alkyl or $C_1$–$C_4$ hydroxyalkyl radical.

The dyeing composition according to the invention can also include various adjuvants conventionally used in hair dyeing compositions, such as anionic, cationic, non-ionic, amphoteric or zwitterionic surface-active agents or their mixtures, anionic, cationic, non-ionic, amphoteric or zwitterionic polymers or their mixtures, inorganic or organic thickening agents, antioxidizing agents, penetration agents, sequestering agents, fragrances, buffers, dispersing agents, conditioning agents, such as, for example, silicones, which are volatile or non-volatile and modified or unmodified, film-forming agents, ceramides, preserving agents or opacifying agents.

Of course, a person skilled in the art will take care to choose this or these optional additional compound or compounds so that the advantageous properties intrinsically attached to the combination in accordance with the invention are not, or not substantially, detrimentally affected by the envisaged addition or additions.

The dyeing composition according to the invention can be provided in various forms, such as in the form of liquids, creams or gels, or in any other form appropriate for carrying out dyeing of keratinous fibres and in particular of human hair.

Another subject-matter of the invention is a process for dyeing keratinous fibres and in particular human keratinous fibres, such as hair, employing the dyeing composition as defined above.

According to this process, the dyeing composition as defined above is applied to the fibres, the colour being developed at acidic, neutral or alkaline pH using an oxidizing agent which is added only at the time of use to the dyeing composition or which is present in an oxidizing composition applied simultaneously or sequentially in a separate fashion.

According to a particularly preferred embodiment of the dyeing process according to the invention, the dyeing composition described above is mixed, at the time of use, with an oxidizing composition comprising, in a medium appropriate for dyeing, at least one oxidizing agent present in an amount sufficient to develop a colouring. The mixture obtained is subsequently applied to the keratinous fibres and is left to stand for 3 to 50 minutes approximately, preferably 5 to 30 minutes approximately, after which the hair is rinsed, washed with a shampoo, rinsed again and dried.

The oxidizing agent present in the oxidizing composition as defined above can be chosen from oxidizing agents conventionally used for the oxidation dyeing of keratinous fibres and among which may be mentioned hydrogen peroxide, urea hydrogen peroxide, alkali metal bromates, persalts, such as perborates and persulphates, or peracids. Hydrogen peroxide is particularly preferred.

The pH of the oxidizing composition including the oxidizing agent as defined above is such that, after mixing with the dyeing composition, the pH of the resulting composition applied to keratinous fibres preferably varies between 3 and 12 approximately and more preferably still between 5 and 11. It is adjusted to the desired value by means of acidifying or basifying agents commonly used in dyeing keratinous fibres and as defined above.

The oxidizing composition as defined above can also include various adjuvants conventionally used in hair dyeing compositions and as defined above.

The composition which is finally applied to keratinous fibres can be provided in various forms, such as in the form of liquids, creams or gels, or in any other form appropriate for carrying out dyeing of keratinous fibres and in particular of human hair.

Another subject-matter of the invention is a dyeing multi-compartment device or kit or any other packaging system with several compartments, a first compartment of which includes the dyeing composition as defined above and a second compartment of which includes the oxidizing composition as defined above. These devices can be equipped with a means allowing the desired mixture to be deposited on the hair, such as the devices disclosed in Patent FR-2,586,913 on behalf of the Applicant Company.

The examples which follow are intended to illustrate the invention without, for all that, limiting the scope thereof.

EXAMPLES

Comparative Dyeing Examples 1 and 2

The following dyeing compositions in accordance with the invention were prepared (contents in grams):

| EXAMPLE | 1 | 2(*) |
|---|---|---|
| 2-Chloro-6-methyl-3-aminophenol (Coupler in accordance with the invention) | 0.236 | 0.236 |
| Pyrazolo[1,5-a]pyrimidine-3,7-diamine dihydrochloride (Oxidation base in accordance with the invention) | 0.333 | — |
| Tetraaminopyrimidine sulphate (Oxidation base not forming part of the invention) | — | 0.357 |
| Common dyeing vehicle No. 1 | () | () |
| Demineralized water, q.s. for | 100 g | 100 g |

(*): Example not forming part of the invention
(**) Common dyeing vehicle No. 1:

| | |
|---|---|
| Oleyl alcohol polyglycerolated with 2 mol of glycerol | 4.0 g |
| Oleyl alcohol polyglycerolated with 4 mol of glycerol comprising 78% of active materials (A.M.) | 5.69 g A.M. |
| Oleic acid | 3.0 g |
| Oleylamine with 2 mol of ethylene oxide, sold under the tradename Ethomeen O12 ® by the company Akzo | 7.0 g |
| Diethylaminopropyl laurylaminosuccinamate, sodium salt, comprising 55% of A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |

-continued

| Propylene glycol monomethyl ether | 9.0 g |
| Sodium metabisulphite as an aqueous solution comprising 35% of A.M. | 0.455 g A.M. |
| Ammonium acetate | 0.8 g |
| Antioxidizing agent, sequestering agent | q.s. |
| Fragrance, preserving agent | q.s. |
| Aqueous ammonia comprising 20% of NH$_3$ | 10.0 g |

It is important to note that each above dyeing composition comprises the same molar amount of oxidation base, namely $1.5 \times 10^{-3}$ mol.

At the time of use, each above dyeing composition was mixed with an equal amount by weight of an oxidizing composition composed of a 20-volume aqueous hydrogen peroxide solution (6% by weight).

Each resulting composition was applied for 30 minutes to locks of natural grey hair comprising 90% of white hairs. The locks of hair were subsequently rinsed, washed with a standard shampoo and then dried.

The locks of hair which were dyed were subsequently subjected to a test of resistance to the effect of shampooing operations.

The colour of the locks of hair dyed with the compositions 1 and 2 was evaluated in the Munsell system by means of a CM 2002 Minolta® calorimeter, before the test of resistance to shampooing operations.

According to the Munsell notation, a colour is defined by the expression H V/C, in which the three parameters respectively denote the tint or Hue (H), the intensity or Value (V) and the purity or Chromaticity (C), the oblique stroke in this expression being simply a convention and not indicating a ratio.

The dyed locks of hair were subsequently subjected to a test of resistance to 6 shampooing operations (Ahiba-Texomat machine).

To do this, the locks of hair were placed in a basket which was immersed in a solution of a standard shampoo at 37° C. The basket was subjected to a vertical to-and-fro movement of variable frequency and to a rotational movement which reproduce the effect of manual rubbing, which leads to the formation of foam.

After testing for 3 minutes, the locks were removed, rinsed and then dried.

The dyed locks were subjected to 6 consecutive shampooing tests.

The colour of the locks was subsequently reevaluated in the Munsell system by means of a CM 2002 Minolta® calorimeter.

The difference between the colour of the lock before the shampooing operations and the colour of the lock after the shampooing operations was calculated by applying the Nickerson formula:

$$\Delta E = 0.4 C_0 \Delta H + 6 \Delta V + 3 \Delta C$$

as described, for example, in "Couleur, Industrie et Technique" [Colour, Industry and Technology], pages 14–17, Vol. No. 5, 1978.

In this formula, $\Delta E$ represents the difference in colour between two locks, $\Delta H$, $\Delta V$ and $\Delta C$ represent the variation in absolute value of the parameters H, V and C, and $C_0$ represents the purity of the lock with respect to which it is desired to evaluate the difference in colour.

The deterioration in the colour increases as the value of $\Delta E$ rises.

The results are given in the table below:

| EXAMPLE | Colour of the hair before the shampooing operations | Colour of the hair after the shampooing operations | Deterioration in the colour | | | |
|---|---|---|---|---|---|---|
| | | | $\Delta H$ | $\Delta V$ | $\Delta C$ | $\Delta E$ |
| 1 | 5.4 R 4.2/5.5 | 4.8 R 4.3/5.0 | 0.6 | 0.1 | 0.5 | 3.4 |
| 2 (*) | 6.3 PB 4.4/1.5 | 1.5 GY 5.0/0.2 | 44.8 | 0.6 | 1.3 | 34.4 |

*Example not forming part of the invention

These results show that the colouring obtained by employing the dyeing composition in accordance with the invention of Example 1, that is to say comprising the specific combination of 2-chloro-6-methyl-3-aminophenol and of pyrazolo[1,5-a]pyrimidine-3,7-diamine, is notably more resistant than the colouring obtained by employing the composition of Example 2, which does not form part of the invention because it comprises the combination of 2-chloro-6-methyl-3-aminophenol and of tetraaminopyrimidine, which is an oxidation base which does not form part of the invention and the use of which with 2-chloro-6-methyl-3-aminophenol is disclosed in Patent Application DE 3,016,008.

Comparative Dyeing Examples 3 and 4

The following dyeing compositions in accordance with the invention were prepared (contents in grams):

| EXAMPLE | 3 | 4 (*) |
|---|---|---|
| 2-Chloro-6-methyl-3-aminophenol (Coupler in accordance with the invention) | 0.471 | 0.471 |
| 2-(β-Hydroxyethyloxy)-para-phenylenediamine dihydrochloride (Oxidation base in accordance with the invention) | 0.723 | — |
| 2-(β-Hydroxyethyl)-para-phenylenediamine dihydrochloride (Oxidation base not forming part of the invention) | — | 0.675 |
| Common dyeing vehicle No. 1 | () | () |
| Demineralized water, q.s. for | 100 g | 100 g |

(*): Example not forming part of the invention
(**) Common dyeing vehicle No. 1: It is identical to that used for Examples 1 and 2 above.

At the time of use, each above dyeing composition was mixed with an equal amount by weight of an oxidizing composition composed of a 20-volume aqueous hydrogen peroxide solution (6% by weight).

Each resulting composition was applied for 30 minutes to locks of permed grey hair comprising 90% of white hairs. The locks of hair were subsequently rinsed, washed with a standard shampoo and then dried.

The colour of the locks was evaluated in the Munsell system by means of a CM 2002 Minolta® calorimeter.

The locks thus dyed were subsequently subjected to a test of resistance to permanent waving.

To do this, the locks were immersed in a commercial reducing solution for permanent waving, comprising 9% by weight of thioglycolic acid, for 15 minutes. The locks were rinsed and the locks of hair were subsequently soaked in a setting solution (8-volume aqueous hydrogen peroxide solution) for 5 minutes. The locks were subsequently rinsed with water, washed with a standard shampoo, rinsed with water and dried.

The colour of the locks was subsequently reevaluated in the Munsell system by means of a CM 2002 Minolta® calorimeter, in order to determine the deterioration in the colouring subsequent to the permanent waving.

The difference between the colour of the lock before the permanent waving and the colour of the lock after the permanent waving was calculated by applying the Nickerson formula:

$$\Delta E = 0.4 C_0 dH + 6 dV + 3 dC$$

as described, for example, in "Couleur, Industrie et Technique" [Colour, Industry and Technology], pages 14–17, Vol. No. 5, 1978.

The deterioration in the colour increases as the value of $\Delta E$ rises.

The results appear in the table below:

dance with the invention, that is to say comprising the specific combination of 2-chloro-6-methyl-3-aminophenol and of 2-(β-hydroxyethyloxy)-para-phenylenediamine, exhibits much better resistance to the effect of the permanent waving than the colouring obtained by employing the composition of Example 4, which does not form part of the invention because it comprises the combination of 2-chloro-6-methyl-3-aminophenol and of 2-(β-hydroxyethyl)-para-phenylenediamine, which is an oxidation base which does not form part of the invention and the use of which with 2-chloro-6-methyl-3-aminophenol is disclosed in Patent Application WO 96/15765.

Dyeing Examples 5 to 10

The following dyeing compositions in accordance with the invention were prepared (contents in grams):

| COMPOSITION | Colour of the hair before the permanent waving | Colour of the hair after the permanent waving | Deterioration in the colouring | | | |
|---|---|---|---|---|---|---|
| | | | $\Delta H$ | $\Delta V$ | $\Delta C$ | $\Delta E$ |
| 3 | 9.9 PB 2.0/3.1 | 2.1 P 2.7/3.3 | 2.2 | 0.7 | 0.2 | 7.5 |
| 4 (*) | 4.9 P 2.0/2.4 | 9.9 P 3.2/2.7 | 5.0 | 1.2 | 0.3 | 12.9 |

*Example not forming part of the invention

These results show that the colouring obtained by employing the dyeing composition of Example 3 in accor-

| | EXAMPLE | | | | | |
|---|---|---|---|---|---|---|
| | 5 | 6 | 7 | 8 | 9 | 10 |
| 2-Chloro-6-methyl-3-aminophenol (coupler) | 0.471 | 0.471 | 0.471 | 0.471 | 0.471 | 0.471 |
| N,N'-Bis(β-hydroxyethyl)-N,N'-bis(4'-aminophenyl)-1,3-diaminopropanol tetrahydrochloride (oxidation base) | 1.518 | — | — | — | — | — |
| ortho-Aminophenol (oxidation base) | — | 0.327 | — | — | — | — |
| Pyrazolo[1,5-a]pyrimidine-3,7-diamine dihydrochloride (oxidation base) | — | — | 0.666 | 0.666 | — | — |
| 2,6-Dimethyl-para-phenylenediamine dihydrochloride (oxidation base) | — | — | — | — | 0.627 | — |
| 2-(β-Hydroxyethyloxy)-para-phenylenediamine dihydrochloride (oxidation base) | — | — | — | — | — | 0.723 |
| Common dyeing vehicle No. 2 | (*) | (*) | (*) | — | (*) | (***) |
| Common dyeing vehicle No. 3 | — | — | — | (****) | — | — |
| Demineralized water, q.s. for | 100 g | 100 g | 100 g | 100 g | 100 g | 100 g |

(***) Common dyeing vehicle No. 2:

| | |
|---|---|
| 96° Ethanol | 18 g |
| Sodium metabisulphite as a 35% aqueous solution | 0.68 g |
| Pentasodium salt of diethylenetriaminopentaacetic acid | 1.1 g |
| Aqueous ammonia comprising 20% of $NH_3$ | 10 g |

(****) Common dyeing vehicle No. 3:

| | |
|---|---|
| 96° Ethanol | 18 g |
| Sodium metabisulphite as a 35% aqueous solution | 0.68 g |
| Pentasodium salt of diethylenetriaminopentaacetic acid | 1.1 g |
| $K_2HPO_4/KH_2PO_4$ (1.5 M/1 M) buffer | 10 g |

At the time of use, each above dyeing composition was mixed with an equal amount by weight of an oxidizing composition composed of a 20-volume aqueous hydrogen peroxide solution (6% by weight).

Each resulting composition was applied for 30 minutes to locks of natural grey hair comprising 90% of white hairs. The locks of hair were subsequently rinsed, washed with a standard shampoo and then dried.

The shades obtained appear in the table below:

| EXAMPLE | DYEING pH | SHADE OBTAINED |
|---|---|---|
| 5 | 10 ± 0.2 | Blue |
| 6 | 10 ± 0.2 | Coppery golden |
| 7 | 10 ± 0.2 | Strong iridescent red |
| 8 | 6.8 ± 0.2 | Strong red |
| 9 | 10 ± 0.2 | Strong deep-purple |
| 10 | 10 ± 0.2 | Strong deep-purple |

What is claimed is:

1. A composition for the oxidation dyeing of keratinous fibers wherein said composition comprises, in a medium suitable for dyeing,
at least one coupler chosen from 2-chloro-6-methyl-3-aminophenol and acid addition salts thereof; and
at least one oxidation base chosen from
(a) paraphenylenediamines of formula (I) and acid addition salts thereof:

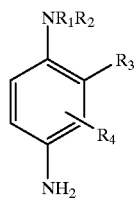

(I)

in which:
$R_1$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)-alkyl radicals, and $C_1$–$C_4$ alkyl radicals substituted by a nitrogenous, phenyl or 4'-aminophenyl group;
$R_2$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)-alkyl radicals and $C_1$–$C_4$ alkyl radicals substituted by a nitrogenous group;
$R_3$ is chosen from a hydrogen atom, $C_1$–$C_4$ alkyl radicals, $C_1$–$C_4$ monohydroxyalkoxy radicals, $C_1$–$C_4$ mesylaminoalkoxy radicals, $C_1$–$C_4$ acetylaminoalkoxy radicals, $C_1$–$C_4$ carbamoylaminoalkoxy radicals and $C_1$–$C_4$ alkyl radicals substituted by a nitrogenous group;
$R_4$ is chosen from a hydrogen atom and $C_1$–$C_4$ alkyl radicals;
with the proviso that:
at least one of the $R_1$, $R_2$, $R_3$ and $R_4$ radicals is other than a hydrogen atom,
when the $R_1$, $R_2$ and $R_4$ radicals simultaneously represent a hydrogen atom, then the $R_3$ radical is other than a methyl radical,
when the $R_1$, $R_2$ and $R_3$ radicals simultaneously represent a hydrogen atom and when the $R_4$ radical occupies the 6 position, then $R_4$ is other than a methyl radical,
when one of the $R_1$ and $R_2$ radicals represents a $C_1$–$C_4$ alkyl radical or a $C_1$–$C_4$ monohydroxyalkyl radical and when the other $R_1$ or $R_2$ radical represents a hydrogen atom, then at least one of the $R_3$ and $R_4$ radicals is other than a hydrogen atom;
when $R_1$ and $R_2$ simultaneously represent a $C_1$–$C_4$ monohydroxyalkyl radical, then at least one of the $R_3$ and $R_4$ radicals is other than a hydrogen atom;
when $R_3$ and $R_4$ simultaneously represent a hydrogen atom, and when one of $R_1$ and $R_2$ is a $C_1$–$C_4$ alkyl radical, the other radical $R_1$ or $R_2$ is not a $C_1$–$C_4$ alkoxy($C_1$–$C_4$)alkyl radical; and
with the proviso that the paraphenylenediamines of formula (I) are not N-Ethyl-N-β-hydroxyethyl-p-phenylenediamine or N,N-dimethyl-p-phenylenediamine;
(b) double bases of formula (II) and acid addition salts thereof:

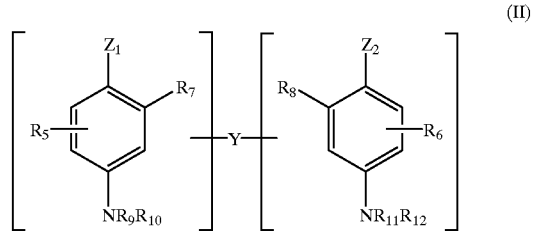

(II)

in which:
$Z_1$ and $Z_2$, which are identical or different, are chosen from a hydroxyl radical and —$NH_2$ radicals which can be substituted by a $C_1$–$C_4$ alkyl radical or by a connecting arm Y;
the connecting arm Y is chosen from linear and branched alkylene chains comprising from 1 to 14 carbon atoms which can be interrupted by at least one entity chosen from nitrogenous groups and heteroatoms and which is optionally substituted by at least one radical selected from hydroxyl and $C_1$–$C_6$ alkoxy radicals;
$R_5$ and $R_6$ is chosen from a hydrogen atom, a halogen atom, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals and a connecting arm Y;
$R_7$, $R_8$, $R_9$, $R_{10}$, $R_{11}$ and $R_{12}$, which are identical or different, are chosen from a hydrogen atom, a connecting arm Y and $C_1$–$C_4$ alkyl radicals;
with the proviso that the compounds of formula (II) only comprise a single connecting arm Y per molecule;
(c) pyrazolo[1,5-a]pyrimidines of formula (III) and acid and base addition salts thereof and tautomeric forms thereof, when a tautomeric equilibrium exists:

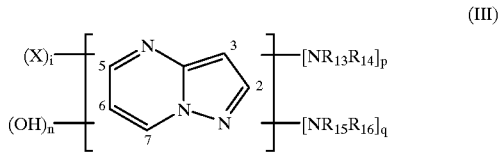

(III)

in which:
$R_{13}$, $R_{14}$, $R_{15}$ and $R_{16}$, which are identical or different, are chosen from a hydrogen atom, $C_1$–$C_4$ alkyl radicals, aryl radicals, $C_1$–$C_4$ hydroxyalkyl radicals, $C_2$–$C_4$ polyhydroxyalkyl radicals, ($C_1$–$C_4$)alkoxy($C_1$–$C_4$)

alkyl radicals, $C_1$–$C_4$ aminoalkyl radicals wherein the amine is optionally protected by an acetyl, amido or sulphonyl radical, ($C_1$–$C_4$)alkylamino($C_1$–$C_4$)alkyl radicals, di(($C_1$–$C_4$)alkyl) amino($C_1$–$C_4$)alkyl radicals wherein the dialkyls optionally form a carbonaceous ring or a heterocycle with 5 or 6 ring members, hydroxy($C_1$–$C_4$)alkylamino($C_1$–$C_4$)alkyl radicals and di(hydroxy($C_1$–$C_4$)alkyl)amino($C_1$–$C_4$)alkyl radicals;

the X radicals, which are identical or different, are chosen from a hydrogen atom, $C_1$–$C_4$ alkyl radicals, aryl radicals, $C_1$–$C_4$ hydroxyalkyl radicals, $C_2$–$C_4$ polyhydroxyalkyl radicals, $C_1$–$C_4$ aminoalkyl radicals, ($C_1$–$C_4$)alkylamino($C_1$–$C_4$)alkyl radicals, di(($C_1$–$C_4$)alkyl)amino($C_1$–$C_4$)alkyl radicals wherein the dialkyls optionally form a carbonaceous ring or a heterocycle with 5 or 6 ring members, hydroxy($C_1$–$C_4$)alkyl-amino ($C_1$–$C_4$)alkyl radicals, di(hydroxy($C_1$–$C_4$)alkyl)-amino ($C_1$–$C_4$)alkyl radicals, amino radicals, ($C_1$–$C_4$) alkylamino radicals, di(($C_1$–$C_4$)alkyl)amino radicals, halogen atoms, carboxylic acid groups and sulphonic acid groups;

i has the value 0, 1, 2 or 3;
p has the value 0 or 1;
q has the value 0 or 1;
n has the value 0 or 1;

with the provision that:
the sum p+q is other than 0;
when p+q is equal to 2, then n has the value 0 and the $NR_{13}R_{14}$ and $NR_{15}R_{16}$ groups occupy the (2,3), (5,6), (6,7), (3,5) or (3,7) positions;
when p+q is equal to 1, then n has the value 1 and the $NR_{13}R_{14}$ or $NR_{15}R_{16}$ group and the OH group occupy the (2,3), (5,6), (6,7), (3,5) or (3,7) positions;

(d) ortho-aminophenols;
(e) diaminopyridines chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, and 3,4-diaminopyridine;
said composition being devoid of an additional coupler chosen from 4-hydroxyindoline, acid addition salts thereof, 6-hydroxyindoline and acid addition salts thereof.

2. The composition of claim 1 wherein said keratinous fibers are human keratinous fibers.

3. The composition of claim 2 wherein said human keratinous fibers are hair.

4. The composition of claim 1, wherein said $C_1$–$C_4$ alkyl radicals of formulae (I), (II) and (III) are chosen from methyl, ethyl, and propyl, and further wherein the $C_1$–$C_4$ alkoxy radicals of said ($C_1$–$C_4$)alkoxy($C_1$–$C_4$)-alkyl radicals of formulae (I) and (III) are chosen from methyloxy and ethyloxy radicals.

5. The composition of claim 1, wherein said nitrogenous groups of formulae (I) and (II) are chosen from amino radicals, mono($C_1$–$C_4$)alkylamino radicals, di($C_1$–$C_4$) alkylamino radicals, tri($C_1$–$C_4$)alkylamino radicals, monohydroxy($C_1$–$C_4$)alkylamino radicals, imidazolinium radicals and ammonium radicals.

6. The composition of claim 1, wherein said heteroatoms are chosen from oxygen, sulphur and nitrogen atoms.

7. The composition of claim 1, wherein said para-phenylenediamines are chosen from 2,3-dimethyl-para-phenylenediamine, 2,6-dimethyl-para-phenylenediamine, 2,6-diethyl-para-phenylenediamine, 2,5-dimethyl-para-phenylenediamine, N,N-diethyl-para-phenylenediamine, N,N-dipropyl-para-phenylenediamine, 4-amino-1-(N,N-diethylamino)-3-methylbenzene, 4-amino-1-(N,N-bis(β-hydroxyethyl)amino)-3-methylbenzene, 2-isopropyl-para-phenylenediamine, 2-n-propyl-para-phenylenediamine, 2-(β-hydroxyethyloxy)-para-phenylenediamine, N,N-dimethyl-3-methyl-para-phenylenediamine, N-(β,γ-dihydroxypropyl)-para-phenylenediamine, N-(β-methoxyethyl)amino-para-phenylenediamine, 2-(β-acetylaminoethyloxy)-para-phenylenediamine and acid addition salts thereof.

8. The composition of claim 1, wherein said para-phenylenediamines are chosen from 2,6-dimethyl-para-phenylenediamine, 2-n-propyl-para-phenylenediamine, 2-(β-hydroxyethyloxy)-para-phenylenediamine, N-(β-methoxyethyl)amino-para-phenylenediamine, 2-(β-acetylaminoethyloxy)-para-phenylenediamine and acid addition salts thereof.

9. The composition of claim 1, wherein said double bases are chosen from N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-diethyl-N,N'-bis(4'-amino-3'-methylphenyl)ethylenediamine and acid addition salts thereof.

10. The composition of claim 1, wherein said pyrazolo [1,5-a]pyrimidines are chosen from
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxyethyl)amino]ethanol;
2-[(7-aminopyrazolo[1,5-a]pyrimidin-3-yl)(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine; and acid addition salts and tautomeric forms thereof, when there exists a tautomeric equilibrium.

11. The composition of claim 1, wherein said ortho-aminophenols are chosen from 2-aminophenol, 2-amino-5-methylphenol, 2-amino-6-methylphenol, 5-acetamido-2-aminophenol and acid addition salts thereof.

12. The composition of claim 1, wherein said at least one coupler represents from 0.0001 to 5% by weight relative to the total weight of the dyeing composition.

13. The composition of claim 12, wherein said at least one coupler represents from 0.005 to 3% by weight relative to the total weight of the dyeing composition.

14. The composition of claim 1, wherein said at least one oxidation base represents from 0.0005 to 12% by weight relative to the total weight of the dyeing composition.

15. The composition of claim 14, wherein said at least one oxidation base represents from 0.005 to 6% by weight relative to the total weight of the dyeing composition.

16. The composition of claim 1, wherein said composition further comprises at least one other ingredient chosen from additional couplers and direct dyes.

17. The composition of claim 1, wherein said acid addition salts are chosen from hydrochlorides, hydrobromides, sulphates and tartrates, lactates and acetates.

18. The composition of claim 1, wherein said base addition salts are chosen from sodium hydroxide, potassium hydroxide, ammonia and amines.

19. The composition of claim 1, wherein said medium suitable for dyeing comprises water or a mixture of water and at least one organic solvent chosen from lower $C_1$–$C_4$ alkanols, glycerol, glycols and glycol ethers, and aromatic alcohols.

20. The composition of claim 19, wherein said at least one organic solvent is present in a proportion ranging from 1 to 40% by weight approximately relative to the total weight of the dye composition.

21. The composition of claim 20, wherein said at least one organic solvent is present in a proportion ranging from 5 to 30% relative to the total weight of the dye composition.

22. The composition of claim 1, wherein said composition has a pH ranging from 3 to 12.

23. The composition of claim 22, wherein said pH ranges from 5 to 11.

24. The composition of claim 1, wherein said composition additionally contains at least one adjuvant chosen from anionic, cationic, nonionic, amphoteric and zwitterionic surfactants, anionic, cationic, nonionic, amphoteric and zwitterionic polymers, organic and inorganic thickeners, antioxidants, penetration agents, sequestrants, fragrances, buffers, dispersants, conditioners, film forming agents, ceramides, preserving agents and opacifiers.

25. The composition of claim 1, wherein said composition is in the form of a liquid, a cream, a gel or any other form appropriate for dyeing keratinous fibers.

26. The composition of claim 1, wherein said composition further comprises an oxidizing composition comprising, in a medium appropriate for dyeing, at least one oxidizing agent present in an amount sufficient for color development of said keratinous fibers.

27. The composition of claim 26, wherein said oxidizing agent is chosen from hydrogen peroxide, urea peroxide, alkali metal bromates, persalts, and peracids.

28. The composition of claim 26, wherein the pH of said composition comprising said oxidizing composition and said dye composition ranges from 3 to 12.

29. The composition of claim 28, wherein said pH ranges from 5 to 11.

30. The composition of claim 26, wherein said composition is in the form of a liquid, a cream, a gel, or any other form appropriate for carrying out dyeing of keratinous fibres.

31. A method for dyeing keratinous fibers, comprising:
contacting said fibers for a time sufficient to achieve color development, with a dye composition comprising:
at least one coupler chosen from 2-chloro-6-methyl-3-aminophenol and acid addition salts thereof; and
at least one oxidation base chosen from
(a) para-phenylenediamines of formula (I) and acid addition salts thereof:

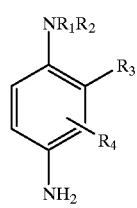

(I)

in which:

$R_1$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)-alkyl radicals and $C_1$–$C_4$ alkyl radicals substituted by a nitrogenous, phenyl or 4'-aminophenyl group;

$R_2$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)-alkyl radicals and $C_1$–$C_4$ alkyl radicals substituted by a nitrogenous group;

$R_3$ is chosen from a hydrogen atom, $C_1$–$C_4$ alkyl radicals, $C_1$–$C_4$ monohydroxyalkoxy radicals, $C_1$–$C_4$ mesylaminoalkoxy radicals, $C_1$–$C_4$ acetylaminoalkoxy radicals, $C_1$–$C_4$ carbamoylaminoalkoxy radicals and $C_1$–$C_4$ alkyl radicals substituted by a nitrogenous group;

$R_4$ is chosen from a hydrogen atom $C_1$–$C_4$ alkyl radicals;

with the proviso that:

at least one of the $R_1$, $R_2$, $R_3$ and $R_4$ radicals is other than a hydrogen atom, when the $R_1$, $R_2$ and $R_4$ radicals simultaneously represent a hydrogen atom, then the $R_3$ radical is other than a methyl radical, when the $R_1$, $R_2$ and $R_3$ radicals simultaneously represent a hydrogen atom and when the $R_4$ radical occupies the 6 position, then $R_4$ is other than a methyl radical, when one of the $R_1$ and $R_2$ radicals represents a $C_1$–$C_4$ alkyl radical or a $C_1$–$C_4$ monohydroxyalkyl radical and when the other $R_1$ or $R_2$ radical represents a hydrogen atom, then at least one of the $R_3$ and $R_4$ radicals is other than a hydrogen atom;

when $R_1$ and $R_2$ simultaneously represent a $C_1$–$C_4$ monohydroxyalkyl radical, then at least one of the $R_3$ and $R_4$ radicals is other than a hydrogen atom;

when $R_3$ and $R_4$ simultaneously represent a hydrogen atom, and when one of $R_1$ and $R_2$ is a $C_1$–$C_4$ alkyl radical, the other radical $R_1$ or $R_2$ is not a $C_1$–$C_4$ alkoxy($C_1$–$C_4$)alkyl radical; and with the proviso that the para-phenylenediamines of formula (I) are not N-Ethyl-N-β-hydroxyethyl-p-phenylenediamine or N,N-dimethyl-p-phenylenediamine;

(b) double bases of formula (II) and acid addition salts thereof:

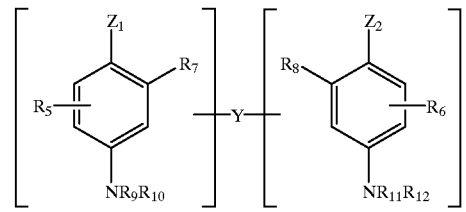

(II)

in which:

$Z_1$ and $Z_2$, which are identical or different, are chosen from hydroxyl and —$NH_2$ radicals which can be substituted by substituent chosen from $C_1$–$C_4$ alkyl radicals and a connecting arm Y;

the connecting arm Y is chosen from linear and branched alkylene chains comprising from 1 to 14 carbon atoms which can be interrupted by at least entity chosen from nitrogenous groups and heteroatoms and which is optionally substituted by at least one radical selected from hydroxyl and $C_1$–$C_6$ alkoxy radicals;

$R_5$ and $R_6$ are chosen from a hydrogen atom, a halogen atom, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals and a connecting arm Y;

$R_7$, $R_8$, $R_9$, $R_{10}$, $R_{11}$ and $R_{12}$, which are identical or different, are chosen from a hydrogen atom, a connecting arm Y and $C_1$–$C_4$ alkyl radicals;

with the proviso that the compounds of formula (II) only comprise a single connecting arm Y per molecule;

(c) pyrazolo[1,5-a]pyrimidines of formula (III) and acid and base addition salts thereof and tautomeric forms thereof, when a tautomeric equilibrium exists:

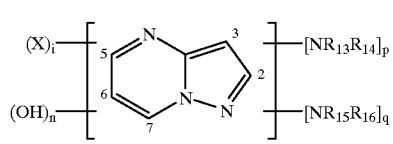

(III)

in which:

$R_{13}$, $R_{14}$, $R_{15}$ and $R_{16}$, which are identical or different, are chosen from a hydrogen atom, $C_1$–$C_4$ alkyl radicals, aryl radicals, $C_1$–$C_4$ hydroxyalkyl radicals, $C_2$–$C_4$ polyhydroxyalkyl radicals, ($C_1$–$C_4$)alkoxy($C_1$–$C_4$) alkyl radicals, $C_1$–$C_4$ aminoalkyl radicals wherein the amine is optionally protected by an acetyl, amido or sulphonyl radical, ($C_1$–$C_4$)alkylamino($C_1$–$C_4$)alkyl radicals, di(($C_1$–$C_4$)alkyl)amino($C_1$–$C_4$)alkyl radicals wherein the dialkyls optionally form a carbonaceous ring or a heterocycle with 5 or 6 ring members, hydroxy($C_1$–$C_4$)alkylamino($C_1$–$C_4$)alkyl radicals, and di(hydroxy($C_1$–$C_4$)alkyl)amino($C_1$–$C_4$)alkyl radicals;

the X radicals, which are identical or different, are chosen from a hydrogen atom, $C_1$–$C_4$ alkyl radicals, aryl radicals, $C_1$–$C_4$ hydroxyalkyl radicals, $C_2$–$C_4$ polyhydroxyalkyl radicals, $C_1$–$C_4$ aminoalkyl radicals, ($C_1$–$C_4$)alkylamino($C_1$–$C_4$)alkyl radicals, di(($C_1$–$C_4$)alkyl)amino($C_1$–$C_4$)alkyl radicals wherein the dialkyls optionally form a carbonaceous ring or a heterocycle with 5 or 6 ring members, hydroxy($C_1$–$C_4$)alkyl-amino ($C_1$–$C_4$)alkyl radicals, di(hydroxy($C_1$–$C_4$)alkyl)-amino ($C_1$–$C_4$)alkyl radicals, amino radicals, ($C_1$–$C_4$) alkylamino radicals, di(($C_1$–$C_4$)alkyl)amino radicals, halogen atoms, carboxylic acid groups and sulphonic acid groups;

i has the value 0, 1, 2 or 3;
p has the value 0 or 1;
q has the value 0 or 1;
n has the value 0 or 1;

with the proviso that:
the sum p+q is other than 0;
when p+q is equal to 2, then n has the value 0 and the $NR_{13}R_{14}$ and $NR_{15}R_{16}$ groups occupy the (2,3), (5,6), (6,7), (3,5) or (3,7) positions;
when p+q is equal to 1, then n has the value 1 and the $NR_{13}R_{14}$ or $NR_{15}R_{16}$ group and the OH group occupy the (2,3), (5,6), (6,7), (3,5) or (3,7) positions;

(d) ortho-aminophenols;
(e) diaminopyridines chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, and 3,4-diaminopyridine;

said composition being devoid of an additional coupler chosen from 4-hydroxyindoline, acid addition salts thereof, 6-hydroxyindoline and acid addition salts thereof, and wherein said dye composition is mixed at the time of said contacting with an oxidizing composition comprising an oxidizing agent present in an amount sufficient for color development.

32. The method of claim 31 wherein said keratinous fibers are human keratin fibers.

33. The method of claim 32 wherein said human keratinous fibers are hair.

34. The method of claim 31, wherein said time sufficient ranges from 3 to 50 minutes.

35. The method of claim 34, wherein said time sufficient ranges from 5 to 30 minutes.

36. The method of claim 31, wherein said at least one oxidizing agent is chosen from hydrogen peroxide, urea peroxide, alkali metal bromates, persalts, and peracids.

37. The method of claim 31, wherein said oxidizing composition including the oxidizing agent, after mixing with the dyeing composition, has a pH ranging from 3 to 12.

38. The method of claim 37, wherein said pH ranges from 5 to 11.

39. The method of claim 31, wherein said oxidizing composition is contacted with said keratinous fibres simultaneously or sequentially with said dye composition.

40. The method of claim 31, wherein said oxidizing composition is contacted with said keratinous fibres separately from said dye composition.

41. The method of claim 31, wherein said oxidizing composition additionally contains at least one adjuvant chosen from anionic, cationic, nonionic, amphoteric and zwitterionic surfactants, anionic, cationic, nonionic, amphoteric and zwitterionic polymers, organic and inorganic thickeners, antioxidants, penetration agents, sequestrants, fragrances, buffers, dispersants, conditioners, film forming agents, ceramides, preserving agents and opacifiers.

42. The method of claim 31, wherein said color development occurs at an acidic, neutral or alkaline pH.

43. The composition of claim 42, wherein said oxidizing method additionally contains at least one adjuvant chosen from anionic, cationic, nonionic, amphoteric and zwitterionic surfactants, anionic, cationic, nonionic, amphoteric and zwitterionic polymers, organic and inorganic thickeners, antioxidants, penetration agents, sequestrants, fragrances, buffers, dispersants, conditioners, film forming agents, ceramides, preserving agents and,opacifiers.

44. A multi-compartment dyeing kit for dyeing keratin fibers, comprising at least two compartments, wherein
a first compartment contains a dye composition comprising:
at least one coupler chosen from 2-chloro-6-methyl-3-aminophenol and acid addition salts thereof; and
at least one oxidation base chosen from
(a) para-phenylenediamines of formula (I) and acid addition salts thereof:

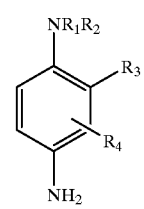

(I)

in which:
$R_1$ is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1-C_4)$alkoxy$(C_1-C_4)$-alkyl radicals and $C_1-C_4$ alkyl radicals substituted by a nitrogenous, phenyl or 4'-aminophenyl group;

$R_2$ is chosen from a hydrogen atom, $C_1-C_4$ alkyl radicals, $C_1-C_4$ monohydroxyalkyl radicals, $C_2-C_4$ polyhydroxyalkyl radicals, $(C_1-C_4)$alkoxy$(C_1-C_4)$-alkyl radicals and $C_1-C_4$ alkyl radicals substituted by a nitrogenous group;

$R_3$ is chosen from a hydrogen atom, $C_1-C_4$ alkyl radicals, $C_1-C_4$ monohydroxyalkoxy radicals, $C_1-C_4$ mesylaminoalkoxy radicals, $C_1-C_4$ acetylaminoalkoxy radicals, $C_1-C_4$ carbamoylaminoalkoxy radicals and $C_1-C_4$ alkyl radicals substituted by a nitrogenous group;

$R_4$ is chosen from a hydrogen atom and $C_1-C_4$ alkyl radicals;

with the proviso that:

at least one of the $R_1$, $R_2$, $R_3$ and $R_4$ radicals is other than a hydrogen atom, when the $R_1$, $R_2$ and $R_4$ radicals simultaneously represent a hydrogen atom, then the $R_3$ radical is other than a methyl radical, when the $R_1$, $R_2$ and $R_3$ radicals simultaneously represent a hydrogen atom and when the $R_4$ radical occupies the 6 position, then $R_4$ is other than a methyl radical, when one of the $R_1$ and $R_2$ radicals represents a $C_1-C_4$ alkyl radical or a $C_1-C_4$ monohydroxyalkyl radical and when the other $R_1$ or $R_2$ radical represents a hydrogen atom, then at least one of the $R_3$ and $R_4$ radicals is other than a hydrogen atom;

when $R_1$ and $R_2$ simultaneously represent a $C_1-C_4$ monohydroxyalkyl radical, then at least one of the $R_3$ and $R_4$ radicals is other than a hydrogen atom when $R_3$ and $R_4$ simultaneously represent a hydrogen atom, and when one of $R_1$ and $R_2$ is a $C_1-C_4$ alkyl radical, the other radical $R_1$ or $R_2$ is not a $C_1-C_4$ alkoxy$(C_1-C_4)$alkyl radical; and with the proviso that the para-phenylenediamines of formula (I) are not N-Ethyl-N-β-hydroxyethyl-p-phenylenediamine or N,N-dimethyl-p-phenylenediamine;

(b) double bases of formula (II) and acid addition salts thereof:

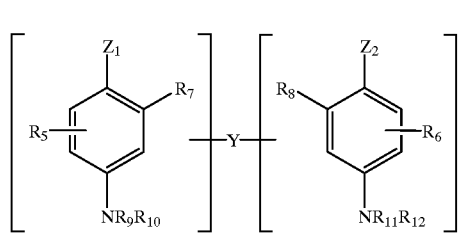

in which:

$Z_1$ and $Z_2$, which are identical or different, are chosen form hydroxyl and —$NH_2$ radicals which can be substituted by a $C_1-C_4$ alkyl radical or by a connecting arm Y;

the connecting arm Y is chosen from linear and branched alkylene chains comprising from 1 to 14 carbon atoms which can be interrupted by at least one entity chosen from nitrogenous groups and heteroatoms and which is optionally substituted by least one radical selected from hydroxyl and $C_1-C_6$ alkoxy radicals;

$R_5$ and $R_6$ are chosen from a hydrogen atom, a halogen atom, $C_1-C_4$ alkyl radicals, $C_1-C_4$ monohydroxyalkyl radicals, $C_2-C_4$ polyhydroxyalkyl radicals, $C_1-C_4$ aminoalkyl radicals and a connecting arm Y;

$R_7$, $R_8$, $R_9$, $R_{10}$, $R_{11}$ and $R_{12}$, which are identical or different, are chosen from a hydrogen atom, a connecting arm Y and $C_1-C_4$ alkyl radicals;

with the proviso that the compounds of formula (II) only comprise a single connecting arm Y per molecule;

(c) pyrazolo[1,5-a]pyrimidines of formula (III) and acid and base addition salts thereof and tautomeric forms thereof, when a tautomeric equilibrium exists:

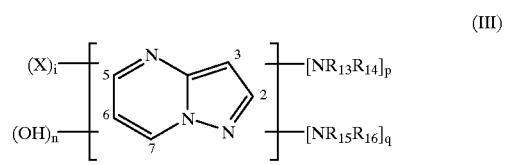

in which:

$R_{13}$, $R_{14}$, $R_{15}$ and $R_{16}$, which are identical or different, are chosen from a hydrogen atom, $C_1-C_4$ alkyl radicals, aryl radicals, $C_1-C_4$ hydroxyalkyl radicals, $C_2-C_4$ polyhydroxyalkyl radicals, $(C_1-C_4)$alkoxy$(C_1-C_4)$alkyl radicals, $C_1-C_4$ aminoalkyl radicals wherein the amine is optionally protected by an acetyl, amido or sulphonyl radical,$(C_1-C_4)$alkylamino$(C_1-C_4)$alkyl radicals, di$((C_1-C_4)$alkyl)amino$(C_1-C_4)$alkyl radicals wherein the dialkyls optionally form a carbonaceous ring or a heterocycle with 5 or 6 ring members, hydroxy$(C_1-C_4)$alkylamino$(C_1-C_4)$alkyl radicals, and di[hydroxy$(C_1-C_4)$alkyl]amino$(C_1-C_4)$alkyl radicals;

the X radicals, which are identical or different, are chosen from a hydrogen atom, $C_1-C_4$ alkyl radicals, aryl radicals, $C_1-C_4$ hydroxyalkyl radicals, $C_2-C_4$ polyhydroxyalkyl radicals, $C_1-C_4$ aminoalkyl radicals, $(C_1-C_4)$alkylamino$(C_1-C_4)$alkyl radicals, di$((C_1-C_4)$alkyl)amino$(C_1-C_4)$alkyl radicals wherein the dialkyls optionally form a carbonaceous ring or a heterocycle with 5 or 6 ring members, hydroxy$(C_1-C_4)$alkylamino$(C_1-C_4)$alkyl radicals, di(hydroxy$(C_1-C_4)$alkyl)amino$(C_1-C_4)$alkyl radicals, amino radicals,$(C_1-C_4)$alkylamino radicals, di$((C_1-C_4)$alkyl)amino radicals, halogen atoms, carboxylic acid groups and sulphonic acid groups;

i has the value 0, 1, 2 or 3;

p has the value 0 or 1;

q has the value 0 or 1;

n has the value 0 or 1;

with the proviso that:

the sum p+q is other than 0;

when p+q is equal to 2, then n has the value 0 and the $NR_{13}R_{14}$ and $NR_{15}R_{16}$ groups occupy the (2,3), (5,6), (6,7), (3,5) or (3,7) positions;

when p+q is equal to 1, then n has the value 1 and the $NR_{13}R_{14}$ or $NR_{15}R_{16}$ group and the OH group occupy the (2,3), (5,6), (6,7), (3,5) or (3,7) positions;

(d) ortho-aminophenols;

(e) diaminopyridines chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, and 3,4-diaminopyridine;

said composition being devoid of an additional coupler chosen from 4-hydroxyindoline, acid addition salts thereof, 6-hydroxyindoline and acid addition salts thereof and a second compartment contains an oxidizing composition.

* * * * *